United States Patent
Crump et al.

(10) Patent No.: US 10,563,288 B2
(45) Date of Patent: Feb. 18, 2020

(54) HIGH PURITY SN-117M COMPOSITIONS AND METHODS OF PREPARING SAME

(71) Applicant: SnIP Holdings, Incorporated, The Woodlands, TX (US)

(72) Inventors: Druce Crump, Lake Jackson, TX (US); Jaime Simon, Angleton, TX (US); St. George George, Pearland, TX (US); Nigel R. Stevenson, Sugar Hill, GA (US)

(73) Assignee: SnIP Holdings, Incorporated, The Woodlands, TX (US)

( * ) Notice: Subject to any disclaimer, the term of this patent is extended or adjusted under 35 U.S.C. 154(b) by 298 days.

(21) Appl. No.: 15/326,104

(22) PCT Filed: Aug. 4, 2015

(86) PCT No.: PCT/US2015/043524
§ 371 (c)(1),
(2) Date: Jan. 13, 2017

(87) PCT Pub. No.: WO2016/022515
PCT Pub. Date: Feb. 11, 2016

(65) Prior Publication Data
US 2017/0204497 A1    Jul. 20, 2017

Related U.S. Application Data

(60) Provisional application No. 62/033,459, filed on Aug. 5, 2014.

(51) Int. Cl.
C22B 3/10    (2006.01)
C22B 25/00    (2006.01)
G21G 1/00    (2006.01)
C22B 3/00    (2006.01)

(52) U.S. Cl.
CPC .............. C22B 25/04 (2013.01); C22B 3/10 (2013.01); G21G 1/001 (2013.01); *G21G 2001/0094* (2013.01)

(58) Field of Classification Search
CPC ............ C22B 3/10; C22B 25/04; G21G 1/001
See application file for complete search history.

(56) References Cited

U.S. PATENT DOCUMENTS 8,632,748 B2    1/2014 Stevenson et al.
9,269,467 B2 *    2/2016 Stevenson ................ G21G 1/10

OTHER PUBLICATIONS

European Patent Office, Extended European Search Report issued in corresponding European Patent Application No. 18171696.0, dated Sep. 4, 2018 (6 pages).
International Search Report and Written Opinion in corresponding PCT/US2015/043524 dated Dec. 28, 2015 (24 pages).
Production of Carrier-Free 117MSN by S.M. Qaim & H. Döhler dated Jul. 1, 1984 (6 pages).
The Production of High Specific Activities of Tin by S Fukushima et al dated Jan. 5, 1963 (4 pages).

* cited by examiner

*Primary Examiner* — Cam N. Nguyen
(74) *Attorney, Agent, or Firm* — Wood Herron & Evans LLP

(57) ABSTRACT

A method of purifying a high specific activity Sn-117m composition is provided that includes extracting an iodide complex of Sn-117m with an organic solvent from an acidic aqueous cadmium solution comprising a dissolved irradiated cadmium target, an acid, and a source of iodide. The organic solvent layer comprising the iodide complex of Sn-117m is substantially reduced in cadmium content. The Sn-117m may be back extracted into an aqueous solution.

13 Claims, No Drawings

HIGH PURITY SN-117M COMPOSITIONS AND METHODS OF PREPARING SAME

PRIORITY CLAIM

This application is a submission under 35 USC § 371 of International Application No. PCT/US2015/043524, filed Aug. 4, 2015, which claims priority to U.S. Provisional Patent Application Ser. No. 62/033,459, filed on Aug. 5, 2014, the disclosures of which are expressly incorporated by reference herein in their entirety.

TECHNICAL FIELD

The present invention is generally directed to high purity Sn-117m compositions and methods of preparing same.

BACKGROUND

The effectiveness of a radiopharmaceutical composition can be improved if the specific activity and purity of a radioisotope is increased. However, specific activity is often limited by the available production methods for the isotope and the subsequent purification procedure. Therefore, a recognized need exists in the art for medically useful radionuclides with high specific activities and purities.

Tin-117m is a useful radioisotope in the field of nuclear medicine. The nuclear-physical and biochemical properties, such as a 14-day half-life, a gamma emission of 158 keV (87%) and a high yield of short-range conversion electrons with energies of 126 keV (64%), 152 keV (26%) and 129 keV (11%), of Sn-117m have been exploited for various bone and joint conditions, including palliative bone cancer treatment.

There are several known methods of producing no-carrier-added (NCA) Sn-117m compositions. For example, reactions utilizing non-tin target atoms may employ proton-induced, $^3$He-particle-induced, or $\alpha$-particle-induced reactions on cadmium and indium targets. Reactions, such as $^{114}$Cd($^3$He, $\gamma$), $^{114}$Cd($\alpha$, n), $^{116}$Cd($^3$He, 2n) $^{116}$Cd($\alpha$, 3n), $^{115}$In(d, $\gamma$), $^{115}$In($^3$He, p), and $^{115}$In($\alpha$, pn), are known to lead to the formation of NCA $^{117m}$Sn. However, in addition to the manner of isotope generation, another major hindrance with producing NCA $^{117m}$Sn with high specific activity is the absence of an effective method for separating $^{117m}$Sn from the target material. Separating small quantities of a desired species from a much larger matrix (debulking) is notoriously difficult using conventional separation methods, such as, chromatography or extraction. Historically, this very aspect of radionuclide purification provoked the use of a carrier, thereby rendering samples with reduced specific activity.

U.S. Pat. Nos. 8,257,681 and 8,632,748, which are incorporated herein by reference in their entirety, disclose extraction and chromatography methods for providing high specific activity, NCA Sn-117m compositions from an irradiated cadmium target. Chromatography methods are generally relatively time intensive, as compared to liquid-liquid extraction methods. However, the disclosed extraction method, which utilized a hexone extraction of a hydrochloric acid solution of the etched irradiated cadmium target, provided a Sn-117m product that still contained a substantial residual quantity of cadmium.

Therefore, in view of the foregoing, there is still a need for new methods for producing high purity, NCA, high specific activity $^{117m}$Sn.

SUMMARY

This invention is premised on the discovery that Sn-117m can be selectively extracted from a bulk cadmium matrix utilizing its iodide complex.

One challenge with producing no-carrier-added (NCA) Sn-117m with high specific activity is the absence of an effective method for separating Sn-117m from the target material. Efficiently separating small quantities of a desired species from a much larger matrix, i.e. debulking, is notoriously difficult using conventional separation methods, such as chromatography or extraction. Historically, this very aspect of radionuclide purification provoked the use of a carrier, thereby rendering samples with reduced specific activity because of dilution by non-radioactive target atoms from the carrier.

Thus, in accordance with an embodiment of the present invention, a method of purifying a high specific activity Sn-117m composition is provided, the method includes: extracting an iodide complex of Sn-117m with an organic solvent from an acidic aqueous cadmium solution comprising a dissolved irradiated cadmium target, an acid, and a source of iodide, to provide an organic solvent layer comprising the iodide complex of Sn-117m.

DETAILED DESCRIPTION OF SPECIFIC EMBODIMENTS

Sn-117m, without the use of a carrier, can be selectively extracted from a bulk cadmium matrix via its iodide complex with an appropriate organic solvent. Thus, a general method of purifying Sn-117m from cadmium, and optionally other metal impurities, has also been has been developed. Thus, while the present invention is not strictly limited by the nuclear reaction that is utilized to produce the Sn-117m composition, the $^{116}$Cd($\alpha$, 3n)$^{117m}$Sn reaction disclosed in U.S. Pat. Nos. 8,257,681 and 8,632,748 that produces high specific activity Sn-117m is an useful method for preparing an irradiated cadmium target containing high specific activity, NCA Sn-117m.

The irradiated cadmium target which contains the Sn-117m is removed from its backing material using an appropriate etchant, such as hydrochloric acid, nitric acid, aqua regia, or other strongly acidic oxidizing solutions. The etchant mixture may be heated to speed up the etching process. The resultant crude etchant solution of the cadmium target comprising Sn-117m may be concentrated by evaporation prior to further processing. Further, the concentrated solution may be diluted or dissolved in the desired acidic medium, such as nitric acid or sulfuric acid.

With or without concentration/dilution, the crude etchant solution is treated with a source of iodide prior to extraction with a suitable organic solvent. Without being bound by any particular theory, the dissolved Sn-117m in an acidic solution forms complexes with iodide. From a chemical perspective, $Sn^{+2}$ and $Sn^{-4}$ readily form $SnI_2$ and $SnI_4$. Exemplary sources of iodide include, but are not limited to, hydrogen iodide (HI) or an iodide salt. Exemplary iodide salts include alkali metal or alkaline earth metal salts. For example, sodium iodide, potassium iodide, or magnesium iodide may be used to form the iodide complex of the Sn-117m. The acidic solution may be formed by using HI. Additionally or alternatively, the crude etchant may be treated with a combination of sulfuric acid and iodide salt. For example, $H_2SO_4$ with NaI may be used to treat the etchant solution to form the iodide complex of Sn-117m. The treated solution may be incubated for a period of time to allow formation of the iodide complex.

Suitable organic solvents include aromatic ring solvents, such as benzene, toluene, xylenes, ethylbenzene, chlorobenzene, or halogenated alkane solvents such as dichlormethane, chloroform, or combinations thereof. The Sn-117m-iodide complex may be extracted by partitioning the acidic iodide-treated solution with a portion of organic solvent. For example, an equal volume of toluene may be mixed with the acidic iodide-treated solution and allowed to separate into organic and aqueous phases. The organic phase, which contains the iodide complex of Sn-117m, can then be separated from the aqueous phase. The organic solvent extraction may be repeated multiple times, if desired.

The organic solvent layer(s) may be combined and the organic solvent removed by evaporation (e.g., stripping on a rotary evaporator) and redissolved in a desired medium, such as 4M HCl prior to further use. The method used to produce and isolate Sn-117m is described in more detail below.

Alternatively, the organic solvent layer(s) may be back-extracted with appropriate HCl solutions, such as 4M HCl. In this embodiment, the Sn-117m is back-extracted from the toluene layer into the 4M HCl solution. The back-extraction process may be repeated multiple times, if desired.

The back-extraction layers may be combined, stripped to remove residual organic solvent, and then taken back up in the appropriate medium prior to further use.

The method used to produce and isolate Sn-117m is described in more detail below.

General Target Preparation

A Cd-116 electroplated copper target may be prepared via the following exemplary process: A Cd-116 solution of highly enriched $^{116}Cd$ may be prepared by dissolving highly enriched Cd-116 in a sulfuric acid solution. The acidic Cd-116 solution may be placed in a plating cell, in contact with a clean copper target. A power supply may be connected to the target solution and the solution electrode such that the negative terminal is attached to the target and the positive terminal is attached to the solution electrode. The copper target may be electroplated with Cd-116 using an electrical current set to a range of about 60 mA to about 100 mA for a sufficient duration of time to provide the desired amount of electroplated Cd-116. The process may be periodically halted to determine the mass of Cd-116 plated on the target.

General NCA $^{117m}Sn$ Production

Irradiation may be performed with about 30 MeV to about 60 MeV α-particles from a cyclotron, (e.g., the MC50 cyclotron at the University of Washington Medical Center in Seattle, Wash.). After bombardment, the irradiated target can be allowed to rest to allow short-lived products to decay away, then the irradiated cadmium target can be subjected to an etching step to remove the cadmium target layer from the copper backing material.

Separation by Liquid-Liquid Extraction

After irradiation, the irradiated cadmium target layer can removed from the copper backing material by dissolving in a etchant solution, such as a heated hydrochloric acid (e.g., 60° C.) or nitric acid solution at room temperature. The etchant solution of the irradiated cadmium target layer is then subsequently treated with a source of iodide and then extracted one or more times with a suitable organic solvent. The etchant solution may be concentrated prior to treatment with iodide. For example, the etchant solution may be concentrated to near dryness and taken back up in the desired acidic solution. The organic solvent layer(s) may be separated from the aqueous layers, combined and back extracted with additional aqueous solutions. This procedure provides for production of Sn-117m having an activity greater than 50 mCi, a specific activity greater than 10,000 Ci/g and metal impurities less than 1 ppm. Further, this provides Sn-117m produced from Cd with a ratio Cd:Sn of less than 1.

The invention will be further appreciated in light of the following detailed examples:

Example 1

Prior Column Purified Sample:
A sample of previously ion exchange column-purified material ($SnCl_4$) that contained elevated levels of residual Cd, Cu, and other metals was purified by taking up the mixture in 3 M $H_2SO_4$; stirring with 20% NaI; extracting with toluene; and back-extracting with 6 M HCl. The toluene layer was analyzed and Cu and Cd were below detectable levels.

Example 2

Irradiated Target Sample:
An irradiated target was etched twice with 2M $HNO_3$ and 1 water wash. The combined solutions were concentrated to 12 mL, split into 3 mL etchant solutions, and then subjected to further processing as follows:

Sample A (63-1):
About 3 mL etchant solution (19.76 mCi Sn-117m) was combined with 3 mL concentrated (57 wt %) HI and then incubated 8 minutes. Some precipitate, which may be $CdI_2$, was observed. The incubated solution was extracted twice with 3 mL portions of toluene. The first toluene extract contained 21.4 mCi Sn-117m, and the second toluene extract contained 1.8 mCi Sn-117m. The combined toluene layers were back-extracted twice with 3 mL portions of 4 M HCl. The first HCl back-extract contained 14.47 mCi Sn-117m, and the second HCl back-extract contained 4.41 mCi Sn-117m. The back-extracts were combined, stripped, taken back up in 1 mL of 4M HCl, and then analyzed to provide 11.98 mCi Sn-117m, 87 ppm Cd, 6.5 ppm Cu, and Fe not detected.

Sample B (63-2):
About 3 mL etch solution (20.11 mCi Sn-117m) was combined with 3 mL concentrated (57 wt %) HI and then incubated for 10 minutes. The incubated solution was extracted twice with 10 mL portions of toluene. The first toluene extract contained 18.13 mCi Sn-117m, and the second toluene extract contained 0.94 mCi Sn-117m. The combined toluene layers were back-extracted twice with 10 mL portions of 4 M HCl. The first HCl back-extract contained 10.66 mCi Sn-117m, and the second HCl back-extract contained 3.33 mCi Sn-117m. The back-extracts were combined, stripped, taken back up in 1 mL of 4 M HCl, and then analyzed to provide 15.8 mCi Sn-117m, 270 ppm Cd, 14 ppm Cu, and a trace Fe.

Sample C (63-3):
About 3 mL etch solution (17.3 mCi Sn-117m) was combined with 3 mL NaI and then incubated for 10 minutes. Extraction of the incubated solution twice with 3 mL portions of toluene removed about 30 uCi of Sn-117m and emulsion formation was significant, though not too hard to break. 2 mL of 3 M $H_2SO_4$ was added to the etch solution and then incubated for 5 minutes. This incubated solution was extracted once with a 3 mL portion of toluene, but only removed about 1 uCi Sn-117m. As such, 5 mL concentrated (57 wt %) HI was added and the solution was again incubated for about 10 minutes. Extraction of this incubated solution was performed with two 5 mL portions of toluene. The first of these toluene extracts contained 14.47 mCi Sn-117m, and the second of these toluene extracts contained 3.71 mCi Sn-117m. These toluene extracts were combined and back-extracted thrice with 3 mL portions of 4 M HCl, where the first back-extract contained 5.01 mCi, the second back-extract contained 5.54 mCi, and the third back-extract contained 2.14 mCi. The back-extracts were combined, stripped, taken back up in 1.2 mL of 4 M HCl, and then analyzed to provide 11.12 mCi of Sn-117m, 14 ppm Cd, 7.5 ppm Cu, and no Fe detectable.

Example 3

(66-1 and 66-2). An irradiated Cd-116 target was etched twice with 10 mL 2 N $HNO_3$ and then rinsed with 10 mL deionized water. The etches and rinse were combined and reduced in volume (rotary evaporator) to 20 mL. A small aliquot of the solution was diluted for Cd and Cu analysis by inductively coupled plasma (ICP) analysis. This solution was divided into two, roughly equal, portions. The results are given in Table 1, below:

TABLE 1

Initial analyses for etches 66-1 and 66-2

| Etch | Mass, g | Activity, mCi | [Cd], ppm | Mass Cd, mg | Cd/Sn, mg/mCi | [Cu], ppm | Mass Cu, mg | Cu/Sn, mg/mCi |
|---|---|---|---|---|---|---|---|---|
| 66-1 | 10.3658 | 73.5 | 40,580 | 420.7 | 5.72 | 2476 | 25.66 | 0.349 |
| 66-2 | 11.9994 | 76.1 | 40,580 | 486.9 | 6.40 | 2476 | 29.71 | 0.390 |

Each of the samples was placed into a 50-mL, plastic centrifuge (Falcon) tube. 10 mL of TraceMetal 57% HI was added, and the resulting solutions were incubated at room temperature (66-1: 15 minutes; 66-2: 35 minutes). Then, 10 mL of HPLC-grade toluene was added to each tube. The tubes were capped and vigorously shaken for one minute. The phases were allowed to separate, and the toluene phases were removed by pipette and collected in another Falcon tube. The Cd/HNO$_3$/HI solutions were then subjected to a second 10 mL toluene extraction. The toluene fractions from each etch were combined.

To each (new) Falcon tube, containing 20 mL toluene solution, was added 15 mL 4 N HCl. The tubes were capped and shaken vigorously for one minute. After the phases were allowed to separate, the (lower) HCl phase was transferred by pipette to another Falcon tube. The HCl back-extraction was repeated, and the HCl phases for each etch solution were combined. To obviate losses due to SnCl$_4$ volatility, the HCl phases were diluted with approximately 200 mL of 2 N HNO$_3$, and the solutions were reduced to near dryness by rotary evaporation. The resulting Sn-117m radiochemical was taken up in approximately 1 mL of 4 N HCl. Final analyses for the radiochemical solutions are given in Table 2 (Sn-117m activities are decay-corrected to the time of the initial etch analyses); yields, specific activities (m Ci Sn-117m activity per mg Sn), and the reduction ratios for Cd and Cu, relative to Sn-117m, are given in Table 3.

TABLE 2

Analytical results for 66-1 and 66-2 products

| Final | Mass, g | Activity, mCi (decay-corrected) | [Cd], ppm | Mass Cd, mg | Cd/Sn, mg/mCi | [Cu], ppm | Mass Cu, mg | Cu/Sn, mg/mCi |
|---|---|---|---|---|---|---|---|---|
| 66-1 | 1.0587 | 51.4 | 39.5 | 0.04182 | 8.535E−4 | 3.1 | 3.282E−3 | 6.698E−5 |
| 66-2 | 1.1640 | 67.8 | 11.5 | 0.01339 | 2.063E−4 | 1.1 | 1.280E−3 | 1.972E−5 |

TABLE 3

Yields, specific activities, and Cd and Cu reduction for 66-1 and 66-2

| Run | Yield, % | Final [Sn], ppm | Mass Sn, mg | Spec. Act., mCi/mg) | Cd Reduction | Cu Reduction |
|---|---|---|---|---|---|---|
| 66-1 | 69.9 | 2.4 | 2.541E−3 | 19,280 | 6700:1 | 5200:1 |
| 66-2 | 89.1 | 2.7 | 3.143E−3 | 20,650 | 31,000:1 | 19,800:1 |

Example 4

(67-1) An irradiated target was etched as described above; but, in this case, the entire etch was reduced in volume to a single, 10 mL solution. 10 mL of 57% HI was added, and the Cd/HI/HNO3 solution was analyzed by ICP. The results are in Table 4:

TABLE 4

Analytical results for etch 67-1

| Etch | Mass, g | Activity, mCi | [Cd], ppm | Mass Cd, mg | Cd/Sn, mg/mCi | [Cu], ppm | Mass Cu, mg | Cu/Sn, mg/mCi |
|---|---|---|---|---|---|---|---|---|
| 67-1 | 39.3904 | 139.4 | 30,080 | 1185 | 8.50 | 1665 | 65.59 | 0.471 |

The mixture was incubated at room temperature for 60 minutes, and then extracted with toluene, then back-extracted with 4 N HCl, as above. The combined HCl fractions were diluted with 2 N HNO3 and stripped by rotary evaporation. The radiochemical was taken up in 1.3 mL 4 N HCl. Analytical results are given in Table 5; yield, specific activity, and reduction ratios are given in Table 6.

TABLE 5

Analytical results for 67-1 product

| Final | Mass, g | Activity, mCi (decay-corrected) | [Cd], ppm | Mass Cd, mg | Cd/Sn, mg/mCi | [Cu], ppm | Mass Cu, mg | Cu/Sn, mg/mCi |
|---|---|---|---|---|---|---|---|---|
| 67-1 | 1.4274 | 113.1 | 36.6 | 0.05224 | 4.741E−4 | 1.6 | 2.284E−3 | 2.072E−5 |

TABLE 6

Yield, specific activity, and Cd and Cu reduction for 67-1

| Run | Yield, % | Final [Sn], ppm | Mass Sn, mg | Spec. Act., mCi/mg) | Cd Reduction | Cu Reduction |
|---|---|---|---|---|---|---|
| 67-1 | 81.2 | 3.8 | 5.424E−3 | 20,850 | 17,900:1 | 22,700:1 |

These examples demonstrate that the present invention provides high specific activity, no-carrier-added Sn-117m with extremely low levels of impurities.

While the present invention has been illustrated by the description of one or more embodiments thereof, and while the embodiments have been described in considerable detail, they are not intended to restrict or in any way limit the scope of the appended claims to such detail. Additional advantages and modifications will readily appear to those skilled in the art. The invention in its broader aspects is therefore not limited to the specific details, representative apparatus and methods and illustrative examples shown and described. Accordingly, departures may be made from such details without departing from the scope or spirit of Applicants' general inventive concept.

What is claimed is:

1. A method of purifying a high specific activity Sn-117m composition, comprising:
   extracting an iodide complex of Sn-117m with an organic solvent from an acidic aqueous cadmium solution, said cadmium solution comprising a dissolved irradiated cadmium target, an acid, and a source of iodide, to provide an organic solvent layer comprising the iodide complex of Sn-117m that is reduced in cadmium content and an acidic cadmium aqueous layer.

2. The method of claim 1, wherein the organic solvent is selected from the group consisting of aromatic ring solvents, halogenated alkane solvents, and mixtures thereof.

3. The method of claim 1, wherein the organic solvent comprises toluene.

4. The method of claim 1, wherein source of iodide is selected from the group consisting of hydrogen iodide, an iodide salt, and mixtures thereof.

5. The method of claim 4, wherein the iodide salt is selected from the group consisting of alkali metal salts, alkaline earth metal salts, and mixtures thereof.

6. The method of claim 1, further comprising:
   dissolving an irradiated cadmium target comprising a quantity of high specific activity Sn-117m to form said cadmium solution.

7. The method of claim 1, further comprising:
   separating the organic solvent layer comprising the iodide complex of Sn-117m from the acidic cadmium aqueous layer to provide an organic solution enriched in Sn-117m.

8. The method of claim 7, further comprising:
   back-extracting the Sn-117m into an acidic solution by washing the organic solvent layer with a hydrochloric acid solution to provide an aqueous solution enriched in Sn-117m that is reduced in cadmium content.

9. The method of claim 8, wherein the hydrochloric acid solution is at least 4M HCl.

10. The method of claim 8, wherein the cadmium content in the aqueous solution enriched in Sn-117m is reduced more than 100 fold relative to the acidic aqueous cadmium solution comprising a dissolved irradiated cadmium target.

11. The method of claim 8, wherein the cadmium content in the aqueous solution enriched in Sn-117m is reduced more than 1000 fold relative to the acidic aqueous cadmium solution comprising a dissolved irradiated cadmium target.

12. The method of claim 8, wherein the aqueous solution enriched in Sn-117m has a Cd-to-Sn mass ratio less than 1.

13. The method of claim 1, wherein the iodide complex of Sn-117m is tin tetraiodide.

* * * * *